(12) United States Patent
Liu

(10) Patent No.: US 10,624,582 B2
(45) Date of Patent: Apr. 21, 2020

(54) ELECTRONIC SKIN AND MANUFACTURING METHOD THEREFOR

(71) Applicant: Guang Dong Dongbond Technology Co., Ltd., Dongguan, Guangdong (CN)

(72) Inventor: Ping Liu, Guangdong (CN)

(73) Assignee: GUANG DONG DONGBOND TECHNOLOGY CO., LTD., Dongguan, Guangdong (CN)

( * ) Notice: Subject to any disclaimer, the term of this patent is extended or adjusted under 35 U.S.C. 154(b) by 176 days.

(21) Appl. No.: 15/618,976

(22) Filed: Jun. 9, 2017

(65) Prior Publication Data

US 2017/0273624 A1 Sep. 28, 2017

Related U.S. Application Data

(63) Continuation of application No. PCT/CN2015/095549, filed on Nov. 25, 2015.

(30) Foreign Application Priority Data

Dec. 12, 2014 (CN) .......................... 2014 1 0770984

(51) Int. Cl.
*H01L 27/12* (2006.01)
*H01L 29/786* (2006.01)
(Continued)

(52) U.S. Cl.
CPC .............. *A61B 5/6813* (2013.01); *A61B 5/01* (2013.01); *A61B 5/02055* (2013.01);
(Continued)

(58) Field of Classification Search
None
See application file for complete search history.

(56) References Cited

U.S. PATENT DOCUMENTS 8,332,053 B1 12/2012 Patterson et al.
2007/0215869 A1* 9/2007 Moriya .................. B82Y 10/00
257/40
(Continued)

FOREIGN PATENT DOCUMENTS

CN 101073125 11/2007
CN 103000530 3/2013
(Continued)

OTHER PUBLICATIONS

International Search Report for priority application, Serial No. PCT/CN2015/095549, dated Mar. 2, 2016, 4 pages. English translation.
(Continued)

*Primary Examiner* — Seahvosh Nikmanesh
*Assistant Examiner* — Xiaoming Liu
(74) *Attorney, Agent, or Firm* — Hamre, Schumann, Mueller & Larson, P.C.

(57) ABSTRACT

An electronic skin is manufactured by disposing an oxide thin film transistor (TFT), a pressure sensor, and a temperature sensor on a flexible substrate. The pressure sensor and the temperature sensor are respectively located on two sides of the flexible substrate. The oxide TFT includes a first TFT and a second TFT. The pressure sensor is configured to drive the first TFT, and the temperature sensor is configured to drive the second TFT. The method for preparing the electronic skin is to form an oxide TFT, a pressure sensor, and a temperature sensor by means of etching and deposition on a flexible substrate whose double sides are covered with conductive materials. The electronic skin provided in the present invention may simultaneously measure pressure and temperatures, and has a simple structure, a low working voltage, small power consumption, high sensitivity, and small interference between sensor signals.

13 Claims, 2 Drawing Sheets

(51) Int. Cl.
*A61B 5/00* (2006.01)
*A61B 5/01* (2006.01)
*A61B 5/22* (2006.01)
*A61B 5/0205* (2006.01)
*A61B 5/024* (2006.01)
*H01L 21/02* (2006.01)
*H01L 21/4757* (2006.01)
*H01L 29/49* (2006.01)
*H01L 29/51* (2006.01)
*H01L 29/66* (2006.01)
*A61B 7/00* (2006.01)

(52) U.S. Cl.
CPC ............ *A61B 5/02438* (2013.01); *A61B 5/22* (2013.01); *A61B 5/222* (2013.01); *H01L 21/0217* (2013.01); *H01L 21/0228* (2013.01); *H01L 21/02164* (2013.01); *H01L 21/02274* (2013.01); *H01L 21/02565* (2013.01); *H01L 21/02631* (2013.01); *H01L 21/47573* (2013.01); *H01L 27/1218* (2013.01); *H01L 27/1225* (2013.01); *H01L 27/1255* (2013.01); *H01L 27/1262* (2013.01); *H01L 29/4908* (2013.01); *H01L 29/512* (2013.01); *H01L 29/518* (2013.01); *H01L 29/66969* (2013.01); *H01L 29/7869* (2013.01); *A61B 5/024* (2013.01); *A61B 7/00* (2013.01); *A61B 2560/0468* (2013.01); *A61B 2562/0247* (2013.01); *A61B 2562/0271* (2013.01); *A61B 2562/06* (2013.01); *A61B 2562/12* (2013.01); *H01L 27/124* (2013.01)

(56) References Cited

U.S. PATENT DOCUMENTS

| | | | |
|---|---|---|---|
| 2012/0138940 A1* | 6/2012 | Sato | .................... H01L 27/1218 |
| | | | 257/59 |
| 2013/0294617 A1 | 11/2013 | Alberth, Jr. | |
| 2014/0339545 A1* | 11/2014 | Yamazaki | ............... H01L 29/24 |
| | | | 257/43 |
| 2015/0207052 A1* | 7/2015 | Carr | .......................... G01J 5/14 |
| | | | 73/1.57 |

FOREIGN PATENT DOCUMENTS

| | | |
|---|---|---|
| CN | 103411710 | 11/2013 |
| CN | 103616097 | 3/2014 |
| CN | 104523285 | 4/2015 |
| TW | 1309195 B | 5/2009 |
| WO | 2013144788 | 10/2013 |
| WO | 2016091070 | 6/2016 |

OTHER PUBLICATIONS

First Office Action of priority Chinese application No. serial No. 201410770984.1, dated May 4, 2016, 7 pages. Chinese with references cited in English.

Krause, Markus et al., PbTiO3/P(VDF-TrFE) nanocomposites for flexible skin. Electrets, 2008. ISE-13. 13th International Symposium, Dec. 31, 2008. 2 pages.

Someya, Takao et al., Cut-and-Paste Organic FET Customized ICs for Application to Artificial Skin. IEEE International Solid-State Circuits Conference Feb. 17, 2004. ISSCC 2004/ Session 16 / TD: Emerging Technologies and Circuits / 16.2, 10 pages.

Zirkl, Martin et al., Low-Voltage Organic Thin-Film Transistors with High-k Nanocomposite Gate Dielectrics for Flexible Electronics and Optothermal Sensors. Advanced Materials: Communication, 2007, vol. 19, pp. 2241-2245.

\* cited by examiner

ELECTRONIC SKIN AND MANUFACTURING METHOD THEREFOR

CROSS REFERENCE TO RELATED APPLICATIONS

This application is a continuation of PCT/CN2015/095549, filed on Nov. 25, 2015. The contents of PCT/CN2015/095549 are all hereby incorporated by reference. PCT/CN2015/095549 claims priority of Chinese application No. 201410770984.1, filed on Dec. 12, 2014.

BACKGROUND

Technical Field

The present disclosure relates to an electronic skin and a manufacturing method therefor.

Related Arts

An electronic skin is prepared by embedding various flexible thin film transistors (TFTs) and various sensors into a soft plastic thin film, and can satisfy large-area requirements of a human body because the electronic skin is soft and thin like a skin and is also an electronic device attached on a skin. The electronic skin not only can sense pressure and temperatures, but also can sense light, humidity, tension, ultrasonic waves, and the like, and can provide feedback in time to human body health data changes by means of real-time monitoring of human body health physiological indexes such as pulses, heartbeats, body temperatures, and muscle group vibrations, and even implement prophase prevention and diagnosis of diseases. Meanwhile, the electronic skin may further be equipped with a memory, and may also have the functions of wireless power supply and wireless data transmission, so that the electronic skin can be carried around, and perform continuous medical signal monitoring for a long time. Therefore, the technology opens a door leading to a micro mobile health monitor. It is necessary to provide a highly-sensitive and durable electronic skin with a simple structure.

SUMMARY

To resolve the foregoing technical problems, the present disclosure provides an electronic skin and a manufacturing method therefor. The electronic skin may simultaneously measure pressure and temperatures, and has a simple structure, a low working voltage, small power consumption, high sensitivity, and small interference between sensor signals.

To achieve the foregoing objectives, the present disclosure uses the following technical solutions:

The present disclosure discloses an electronic skin, where an oxide TFT, a pressure sensor, and a temperature sensor are disposed on a flexible substrate, the pressure sensor and the temperature sensor are respectively located on two sides of the flexible substrate, the oxide TFT includes a first TFT and a second TFT, the pressure sensor is configured to drive the first TFT, and the temperature sensor is configured to drive the second TFT.

Preferably, a material of the flexible substrate is polyimide having a thickness of 10 µm to 50 µm.

Preferably, the first TFT and the second TFT use a same top gate structure, and each of the pressure sensor and the temperature sensor is provided with a corresponding storage capacitor.

Preferably, each of the first TFT and the second TFT includes a drain, a source, a gate, an active layer, a first gate insulation layer, and a second gate insulation layer, and the drain and the source are located on a same layer, the active layer is located on the layer where the corresponding drain and source are located and partially overlaps with the corresponding drain and source, the first insulation layer covers the corresponding active layer, the second insulation layer covers the corresponding drain and source and the first insulation layer, and the gate is located on the corresponding second insulation layer; and the source of the first TFT is connected to the pressure sensor, and the source of the second TFT is connected to the temperature sensor through a through hole of the flexible substrate.

Preferably, the drain, the source, and the gate of each of the first TFT and the second TFT use a metal electrode, a transparent conductive electrode, or a carbon nano-tube, the active layer of each of the first TFT and the second TFT uses a metal oxide semiconductor, the first insulation layer of each of the first TFT and the second TFT uses SiOx, and the second insulation layer of each of the first TFT and the second TFT uses SiNx.

In addition, the present disclosure further discloses a method for preparing an electronic skin, where a first TFT, a second TFT, a pressure sensor, and a temperature sensor are formed, by means of etching and deposition, on a flexible substrate whose double sides are covered with conductive materials, and the pressure sensor and the temperature sensor are respectively formed on two sides of the flexible substrate.

Preferably, the manufacturing method specifically comprises the following steps:

S1: etching a pattern A on one side of the flexible substrate whose double sides are covered with conductive materials, where the pattern A includes a source and a drain of the first TFT and a source and a drain of the second thin film transistor;

S2: etching a pattern B on the other side of the flexible substrate, where the pattern B includes an electrode of the temperature sensor;

S3: drilling a hole at a corresponding position, connected to the pattern B, of the flexible substrate, and electroplating the drilling position, so that the pattern B is electrically connected to the pattern A;

S4: forming a semiconductor layer on the pattern A, then depositing an insulation layer on the semiconductor layer, separately etching active layers of the first TFT and the second TFT on the semiconductor layer, separately etching first insulation layers of the first TFT and the second TFT on the insulation layer, and then depositing second insulation layers on the first insulation layers of the first TFT and the second TFT; and S5: forming a conductive layer on the second insulation layers, and etching gates of the first TFT and the second TFT and the pressure sensor.

Preferably, step S4 specifically includes:

S41: forming a metal oxide semiconductor layer on the pattern A by using a magnetron sputtering method, and then forming an SiOx layer on the metal oxide semiconductor layer by using an ALD method;

S42: respectively etching the first insulation layers of the first TFT and the second TFT on the SiOx layer by using a dry etching process, and respectively etching the active layers of the first TFT and the second TFT on the metal oxide semiconductor layer by using a wet etching process; and S43: forming the second insulation layers of the first TFT and the second TFT on the first insulation layers of the first TFT and the second TFT by using a plasma enhanced chemical vapor deposition method (PECVD), and forming, by using a dry etching method, through holes at corresponding positions where the second insulation layers are connected to the sources.

Preferably, step S5 specifically includes:

S51: forming the conductive layer on the second insulation layers of the first TFT and the second TFT by using a magnetron sputtering method, and etching the gates of the first TFT and the second TFT and lower electrodes of the pressure sensor and the temperature sensor;

S52: forming a passivation layer by using a PECVD method; and

S53: etching a sensitive area of the pressure sensor by using a dry etching process, forming a sensitive layer of the pressure sensor by using a printing method or an ink jet printing method, and then forming an upper electrode of the pressure sensor on the sensitive layer.

Preferably, a distance between the source and the drain of the first TFT is 2 μm to 20 μm and a distance between the source and the drain of the second TFT is 2 μm to 20 μm.

Compared with the prior art, beneficial effects of the present disclosure are that: in the electronic skin provided in the present disclosure, the pressure sensor and the temperature sensor are disposed on two sides of the flexible substrate, so that pressure and temperatures may be simultaneously measured; the electronic skin is flexible, and has a simple structure, a low working voltage, small power consumption, high sensitivity, and small interference between sensor signals.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION

The present disclosure is described in further detail below with reference to embodiments and the accompanying drawings.

Figure 1:
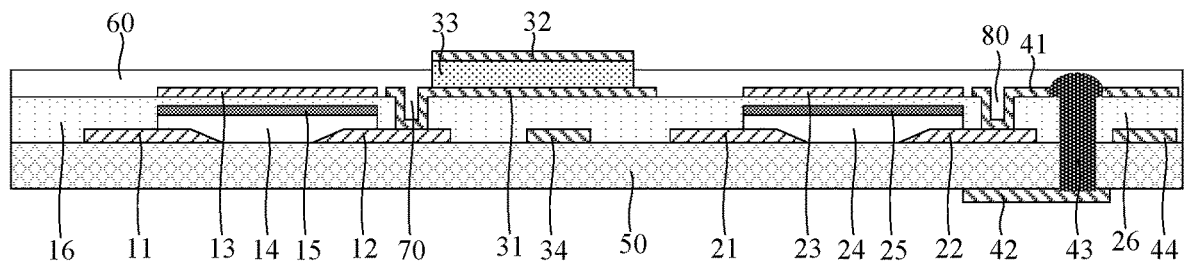
FIG. 1 is a schematic sectional view of an electronic skin according to a preferable embodiment of the present disclosure.

FIG. 1 is a schematic sectional view of an electronic skin according to a preferable embodiment of the present disclosure. The electronic skin includes a flexible substrate 50. A first TFT, a second TFT, a pressure sensor, and a temperature sensor are disposed on the flexible substrate 50. The pressure sensor and the temperature sensor are respectively located on two sides of the flexible substrate. The first TFT is configured to drive the pressure sensor, and the second TFT is configured to drive the temperature sensor. The first TFT includes a drain 11, a source 12, a gate 13, an active layer 14, a first insulation layer 15, and a second insulation layer 16. The second TFT includes a drain 21, a source 22, a gate 23, an active layer 24, a first insulation layer 25, and a second insulation layer 26. The drain 11, the source 12, the drain 21, and the source 22 are located on a same layer. The active layer 14 is located on the layer where the drain 11 and the source 12 are located, and partially overlaps with the drain 11 and the source 12. The active layer 24 is located on the layer where the drain 21 and the source 22 are located and partially overlaps with the drain 21 and the source 22. The first insulation layer 15 covers the active layer 14. The first insulation layer 25 covers the active layer 24. The second insulation layer 16 covers the drain 11, the source 12, and the first insulation layer 15. The second insulation layer 26 covers the drain 21, the source 22, and the first insulation layer 25. The gate 13 is located on the second insulation layer 16. The gate 23 is located on the second insulation layer 26. The pressure sensor includes a lower electrode 31, an upper electrode 32, a pressure sensitive area 33, and an electrode 34. The lower electrode 31 of the pressure sensor is connected to the source 12 of the first TFT through a through hole 70. The lower electrode 31, the second insulation layer 16, and the electrode 34 form a storage capacitor of the pressure sensor. Active areas of the pressure sensitive area 33 and the upper electrode 32 are limited by a passivation layer 60. The temperature sensor includes a lower electrode 41, an electrode 42, a through hole 43, and an electrode 44. The electrode 42 of the temperature sensor is connected to the source 22 of the second TFT through a through hole 80 and the through hole 43. The electrode 44, the second insulation layer 26, and the lower electrode 41 form a storage capacitor of the temperature sensor. Preferably, a material of the flexible substrate is polyimide having a thickness of 10 μm to 50 μm. The drain 11, the source 12, the gate 13, the drain 21, the source 22, the gate 23, the lower electrode 31, the upper electrode 32, the electrode 34, the lower electrode 41, the electrode 42, the electrode 44, and interconnected conductive layers may use a metal electrode, a transparent conductive electrode, conductive nano silver, a carbon nano-tube, and the like. The active layers 14 and 24 may use a metal oxide semiconductor, such as zinc tin oxide (ZTO) or indium gallium zinc oxide (IGZO). The first insulation layers 15 and 25 may use SiOx. The second insulation layers 16 and 26 may use SiNx. The pressure sensitive layer 33 may use a QTC material, a piezoelectric material, a piezoresistive material, or the like. The passivation layer 60 uses SiNx.

Figure 2:
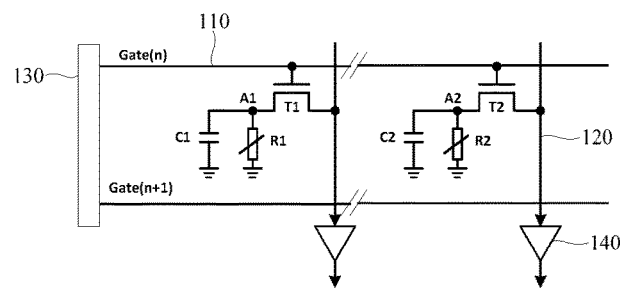
FIG. 2 is an equivalent circuit diagram of a sensor unit.
Figure 3:
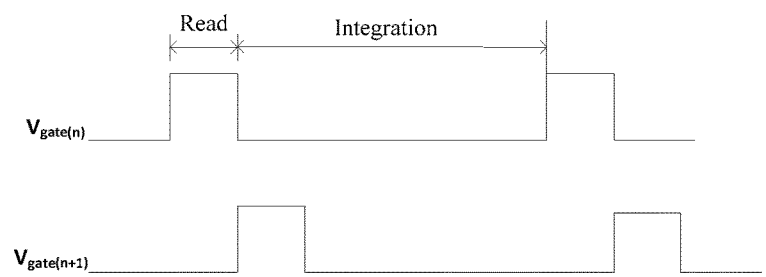
FIG. 3 is a driving pulse diagram of the sensor unit.

A sensor unit of the electronic skin may read, by means of scanning and addressing, electrical signals generated by means of pressure and temperature changes. An equivalent circuit of the sensor unit is shown in FIG. 2, and a corresponding driving pulse is shown in FIG. 3. A row electrode 110 is connected to the gate of the first TFT T1; a signal of a row driver 130 provides a scan pulse Vgate to the first TFT T1 to select a row electrode; the source of the first TFT T1 and the source of the second TFT T2 are connected to a column electrode 120. Equivalently, a pressure sensing unit may be a variable resistor R1. When there is a touch, the size of resistance is relevant to the size of pressure; when there is no touch, the resistance is great, and signals are stored in a capacitor C1. Equivalently, a temperature sensing unit is a variable resistor R2 that changes with temperatures, and signals are stored in a capacitor C2.

With reference to FIG. 2 and FIG. 3, when Vgate is low, the first TFT T1 and the second TFT T2 are cut off, and the pressure sensor and the temperature sensor are both in a signal integration phase. When there is a touch action or when the temperature changes, resistance of the pressure sensing unit or the temperature sensing unit changes, and the corresponding storage capacitor discharges by using the corresponding sensing unit, and a voltage of a node A1 or node A2 changes; when Vgate is high, the first TFT T1 and the second TFT T2 are conducted, and the pressure sensor and the temperature sensor are both in a signal reading phase, and the column electrode 120 charges the capacitor C1 and the capacitor C2 respectively by using the first TFT T1 and the second TFT T2, and charging signals are read by a column amplifier 140.

A method for manufacturing an electronic skin according to a preferable embodiment of the present disclosure includes the following steps.

Figure 4:
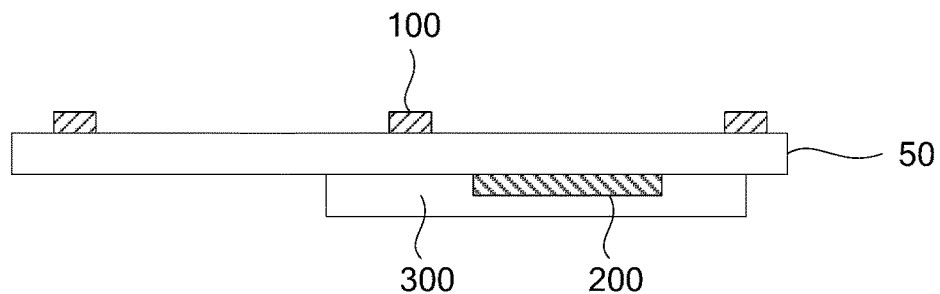
FIG. 4 is a schematic diagram 1 of manufacturing of an electronic skin according to a preferable embodiment of the present disclosure.

As shown in FIG. 4, a flexible substrate 50 whose double sides are covered with conductive materials is first selected. Preferably, the thickness of the flexible substrate is 10 µm to 50 µm. In this embodiment, a polyimide material whose double sides are covered with copper and thickness is 25 µm is selected. A pattern 100 is etched on copper on one side of the flexible substrate 50, and the pattern 100 represents a source and a drain of a TFT, an electrode of a capacitor, a row electrode (data line), a column electrode (scanning line), interconnected conductive wires, and the like of. A pattern 200 is etched on copper on the other side of the flexible substrate 50, and the pattern 200 represents an electrode and the like of a temperature sensor.

Figure 5:
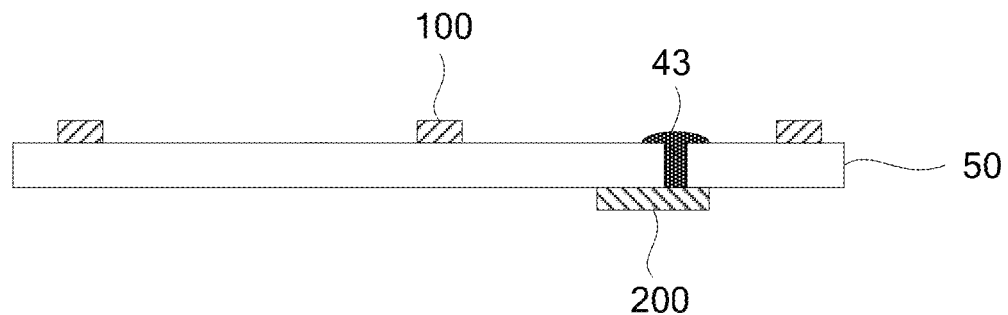
FIG. 5 is a schematic diagram 2 of manufacturing of an electronic skin according to a preferable embodiment of the present disclosure.

As shown in FIG. 5, then the pattern 200 is protected by using an adhesive 300. A hole is drilled at a corresponding position, connected to the pattern 200, of the flexible substrate 50. The aperture is preferably 10 µm to 50 µm. Then electroplating is performed to form a through hole 43, and the adhesive 300 is removed.

Figure 6:
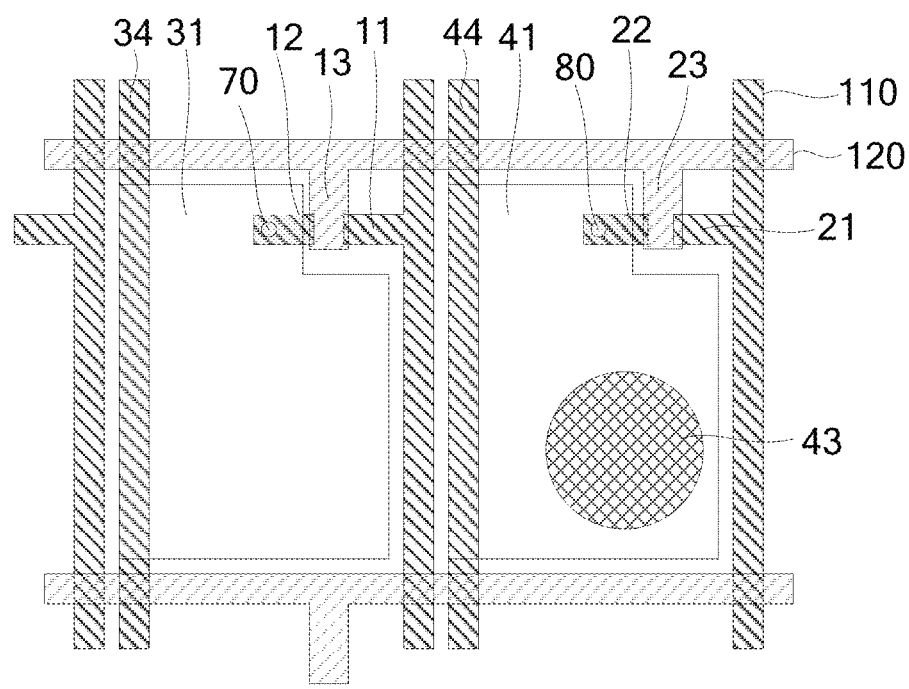
FIG. 6 is a top view in a manufacturing process of an electronic skin according to a preferable embodiment of the present disclosure.

FIG. 6 is a top view of the flexible substrate 50 including a first TFT and a second TFT. It is seen from FIG. 6 that copper on the flexible substrate 50 is etched to form: a source 12 and a drain 11 of the first TFT, a source 22 and a drain 21 of the second TFT, a row electrode (data line) 120 connected to both the drains 11 and 21, an electrode 34 of a storage capacitor C1 and an electrode 44 of a storage capacitor C2, and the through hole 43 formed by electroplating. The width of a channel between the source 12 and the drain 11 of the first TFT is 2 µm to 20 µm, and is preferably 10 µm, so as to satisfy the feature of flexibility of the electronic skin.

With reference to FIG. 1, FIG. 5, and FIG. 6, a semiconductor layer, such as ZTO and IGZO, is formed on the etched pattern 100 by using a magnetron sputtering method. Preferably, the thickness is 40 to 60 nm. An SiOx layer is deposited by using an ALD method. Preferably, the thickness is 20 nm. Then a first insulation layer 15 of the first TFT and a second insulation layer 25 of the second TFT are formed by using a dry etching process; and an active layer 14 of the first TFT and an active layer 24 of the second TFT are formed by using a wet etching process. An SiNx layer is deposited on the first insulation layer 15 of the first TFT and on the first insulation layer 25 of the second TFT by using a PECVD method. Preferably, the thickness is 80 nm to 200 nm, that is, a second insulation layer 16 of the first TFT and a second insulation layer 26 of the second TFT are simultaneously formed. A through hole 70 and a through hole 80 are formed by using a dry etching process. Then a conductive layer is formed by using a magnetron sputtering method.

The formed conductive layer is etched to form: a gate 13 of the first TFT, a gate 23 of the second TFT, a column electrode (scanning line) 120 connected to the gates 13 and 23, a lower electrode 31 of the pressure sensor, and a lower electrode 41 of the temperature sensor. The lower electrode 31 of the pressure sensor is connected to the source 12 of the first TFT through the through hole 70. The lower electrode 31 of the pressure sensor and the electrode 34 form the storage capacitor C1. The lower electrode 41 of the temperature sensor is connected to the source 22 of the second TFT through the through hole 80, and is also connected to the temperature sensor below the flexible substrate 50 through the through hole 43. The lower electrode 41 of the temperature sensor and the electrode 44 form a storage capacitor C2.

Finally, a passivation layer 60 is formed by using a PECVD method. A sensitive area of the pressure sensor is formed by using a dry etching method. A pressure sensitive layer 33 is formed by using a printing method and an ink jet printing method, and then an upper electrode 32 of the pressure sensor is formed by using a magnetron sputtering method.

Figure 7:
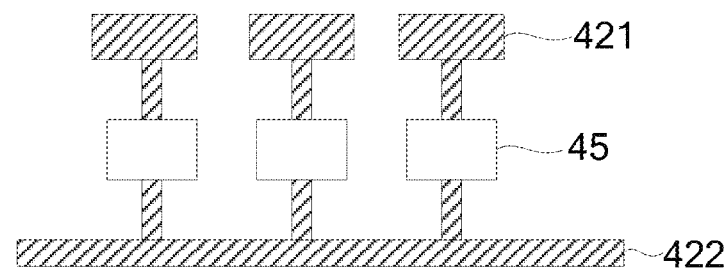
FIG. 7 is a schematic diagram of a connection of a temperature sensor of an electronic skin according to a preferable embodiment of the present disclosure.

The temperature sensor may use a stacking method. However, flexibility of the manner is relatively poor. Therefore, a temperature sensor shown in FIG. 7 is used in this preferable embodiment of the present disclosure. Electrodes 421 and 422 are both connection wires of the temperature sensor, that is, both correspond to the electrode 42 of the temperature sensor shown in FIG. 1. The electrode 421 is connected to the source of the second TFT. There may be multiple choices for the temperature sensor. A thermistor 45 is used in this preferable embodiment of the present disclosure, and the thermistor 45 is connected to the electrodes 421 and 422 within a plane.

The electronic skin provided in the present disclosure is an electronic skin based on an oxide TFT. The electronic skin includes a flexible substrate, an oxide TFT, a pressure sensor, and a temperature sensor. The oxide TFT includes a first TFT and a second TFT. The first TFT and the second TFT use a same top gate structure, and are formed at a time in process. A source of the first TFT is connected to the pressure sensor; the first TFT becomes a signal reading mechanism of the pressure sensor; pressure signals are stored in a corresponding storage capacitor; a source of the second TFT is connected to the temperature sensor through a through hole on the flexible substrate; the second TFT becomes a signal reading mechanism of the temperature sensor, and temperature change signals are stored in a corresponding storage capacitor. In addition, the pressure sensor and the temperature sensor are located in a same TFT array, and the pressure change signals and the temperature change signals are read by using a row electrode (data line) by using a same scanning reading pulse.

The electronic skin prepared by using the manufacturing method of the present disclosure implements the function of simultaneously measuring pressure and temperatures, may be used in detection of human pulses, heartbeats, intraocular pressure, muscular movement, and the like, and may also be used in detection of body temperatures or environmental temperatures.

Although the present disclosure is described above in further detail with reference to specific preferable implementation manners, it should not be considered that the present disclosure is merely limited to the specific implementation manners. Several equivalent replacements or obvious variations with the same performance or purpose may be further made without departing from the spirit of the present disclosure by a person skilled in the art to which the present disclosure belongs shall fall within the protection scope of the present disclosure.

What is claimed is:

1. An electronic skin, wherein an oxide thin film transistor (TFT), a pressure sensor, and a temperature sensor are disposed on a flexible substrate, the pressure sensor and the temperature sensor are respectively located on two sides of the flexible substrate, the oxide TFT comprises a first TFT and a second TFT, the pressure sensor is configured to drive the first TFT, and the temperature sensor is configured to drive the second TFT,
 wherein the first TFT and the second TFT use a same top gate structure, and each of the pressure sensor and the temperature sensor is provided with a corresponding storage capacitor,
 wherein a row electrode is connected to a gate of the first TFT and a gate of the second TFT, a row driver provides a scan pulse Vgate to the first TFT and the second TFT via the row electrode, a source of the first TFT and a source of the second TFT are connected to a column electrode; when Vgate is low, the first TFT and the second TFT are cut off, and the pressure sensor and the temperature sensor are both in a signal integration phase, when there is a touch action or when the temperature changes, the corresponding storage capacitor of the pressure sensing unit or the temperature sensing unit discharges; when Vgate is high, the first TFT and the second TFT are conducted, and the pressure sensor and the temperature sensor are both in a signal reading phase, and the column electrode charges the corresponding storage capacitor and charging signals are read by a column amplifier.

2. The electronic skin according to claim 1, wherein a material of the flexible substrate is polyimide having a thickness of 10 μm to 50 μm.

3. The electronic skin according to claim 1, wherein each of the first TFT and the second TFT comprises a drain, a source, a gate, an active layer, a first gate insulation layer, and a second gate insulation layer, and
 the drain and the source are located on a same layer, the active layer is located on the layer where the corresponding drain and source are located and partially overlaps with the corresponding drain and source, the first insulation layer covers the corresponding active layer, the second insulation layer covers the corresponding drain and source and the first insulation layer, and the gate is located on the corresponding second insulation layer; and
 the source of the first TFT is connected to the pressure sensor, and the source of the second TFT is connected to the temperature sensor through a through hole of the flexible substrate.

4. The electronic skin according to claim 3, wherein the drain, the source, and the gate of each of the first TFT and the second TFT use a metal electrode, a transparent conductive electrode, or a carbon nano-tube, the active layer of each of the first TFT and the second TFT uses a metal oxide semiconductor, the first insulation layer of each of the first TFT and the second TFT uses SiOx, and the second insulation layer of each of the first TFT and the second TFT uses SiNx.

5. A method for manufacturing the electronic skin of claim 1, wherein a first thin film transistor (TFT), a second TFT, a pressure sensor, and a temperature sensor are formed, by means of etching and deposition, on a flexible substrate whose double sides are covered with conductive materials, and the pressure sensor and the temperature sensor are respectively formed on two sides of the flexible substrate.

6. The manufacturing method according to claim 5, wherein the manufacturing method specifically comprises the following steps:
 S1: etching a pattern A on one side of the flexible substrate whose double sides are covered with conductive materials, wherein the pattern A comprises a source and a drain of the first TFT and a source and a drain of the second TFT;
 S2: etching a pattern B on the other side of the flexible substrate, wherein the pattern B comprises an electrode of the temperature sensor;
 S3: drilling a hole at a corresponding position, connected to the pattern B, of the flexible substrate, and electroplating the drilling position, so that the pattern B is electrically connected to the pattern A;
 S4: forming a semiconductor layer on the pattern A, then depositing an insulation layer on the semiconductor layer, separately etching active layers of the first TFT and the second TFT on the semiconductor layer, separately etching first insulation layers of the first TFT and the second TFT on the insulation layer, and then depositing second insulation layers on the first insulation layers of the first TFT and the second TFT; and
 S5: forming a conductive layer on the second insulation layers, and etching gates of the first TFT and the second TFT and the pressure sensor.

7. The manufacturing method according to claim 6, wherein step S4 specifically comprises:
 S41: forming a metal oxide semiconductor layer on the pattern A by using a magnetron sputtering method, and then forming an SiOx layer on the metal oxide semiconductor layer by using an atomic layer deposition (ALD) method;
 S42: respectively etching the first insulation layers of the first TFT and the second TFT on the SiOx layer by using a dry etching process, and respectively etching the active layers of the first TFT and the second TFT on the metal oxide semiconductor layer by using a wet etching process; and
 S43: forming the second insulation layers of the first TFT and the second TFT on the first insulation layers of the first TFT and the second TFT by using a plasma enhanced chemical vapor deposition (PECVD) method, and forming, by using a dry etching method, through holes at corresponding positions where the second insulation layers are connected to the sources.

8. The manufacturing method according to claim 6, wherein step S5 specifically comprises:
 S51: forming the conductive layer on the second insulation layers of the first TFT and the second TFT by using a magnetron sputtering method, and etching the gates of the first TFT and the second TFT and lower electrodes of the pressure sensor and the temperature sensor;
 S52: forming a passivation layer by using a PECVD method; and
 S53: etching a sensitive area of the pressure sensor by using a dry etching process, forming a sensitive layer of the pressure sensor by using a printing method or an ink jet printing method, and then forming an upper electrode of the pressure sensor on the sensitive layer.

9. The manufacturing method according to claim 7, wherein step S5 specifically comprises:
 S51: forming the conductive layer on the second insulation layers of the first TFT and the second TFT by using a magnetron sputtering method, and etching the gates of the first TFT and the second TFT and lower electrodes of the pressure sensor and the temperature sensor;

S52: forming a passivation layer by using a PECVD method; and

S53: etching a sensitive area of the pressure sensor by using a dry etching process, forming a sensitive layer of the pressure sensor by using a printing method or an ink jet printing method, and then forming an upper electrode of the pressure sensor on the sensitive layer.

10. The manufacturing method according to claim 6, wherein a distance between the source and the drain of the first TFT is 2 μm to 20 μm, and a distance between the source and the drain of the second TFT is 2 μm to 20 μm.

11. The manufacturing method according to claim 7, wherein a distance between the source and the drain of the first TFT is 2 μm to 20 μm, and a distance between the source and the drain of the second TFT is 2 μm to 20 μm.

12. The manufacturing method according to claim 8, wherein a distance between the source and the drain of the first TFT is 2 μm to 20 μm, and a distance between the source and the drain of the second TFT is 2 μm to 20 μm.

13. The manufacturing method according to claim 9, wherein a distance between the source and the drain of the first TFT is 2 μm to 20 μm, and a distance between the source and the drain of the second TFT is 2 μm to 20 μm.

\* \* \* \* \*